United States Patent
Grey et al.

(10) Patent No.: US 6,498,259 B1
(45) Date of Patent: Dec. 24, 2002

(54) DIRECT EPOXIDATION PROCESS USING A MIXED CATALYST SYSTEM

(75) Inventors: Roger A. Grey, West Chester, PA (US); C. Andrew Jones, Newtown Square, PA (US)

(73) Assignee: Arco Chemical Technology L.P., Greenville, DE (US)

( * ) Notice: Subject to any disclaimer, the term of this patent is extended or adjusted under 35 U.S.C. 154(b) by 0 days.

(21) Appl. No.: 10/046,502

(22) Filed: Oct. 19, 2001

(51) Int. Cl.[7] .............................................. C07D 301/06
(52) U.S. Cl. .................. 549/533; 549/532; 549/523
(58) Field of Search ................. 549/533, 532, 549/523

(56) References Cited

U.S. PATENT DOCUMENTS

| | | | |
|---|---|---|---|
| 3,351,635 A | 11/1967 | Kollar | 260/348.5 |
| 4,367,342 A | 1/1983 | Wulff et al. | 549/529 |
| 4,833,260 A | 5/1989 | Neri et al. | 549/531 |
| 5,623,090 A | 4/1997 | Haruta et al. | 568/360 |
| 6,008,388 A | 12/1999 | Dessau et al. | 549/531 |
| 6,307,073 B1 | 10/2001 | Jones | 549/532 |

FOREIGN PATENT DOCUMENTS

| | | |
|---|---|---|
| JP | 4-352771 | 12/1992 |
| WO | WO 98/00413 | 6/1997 |

*Primary Examiner*—Ba K. Trinh
(74) *Attorney, Agent, or Firm*—Kevin M. Carroll

(57) ABSTRACT

The liquid-phase epoxidation reaction of an olefin with hydrogen and oxygen in the presence of a catalyst mixture containing a titanium zeolite and a supported catalyst surprisingly produces less ring-opened products such as glycols when performed in the presence of a buffer. This is particularly surprising because a typical palladium on titanium zeolite catalyst is little effected by the presence of a buffer. Surprisingly, the use of a buffer also typically improves the activity of the process.

20 Claims, No Drawings

DIRECT EPOXIDATION PROCESS USING A MIXED CATALYST SYSTEM

FIELD OF THE INVENTION

This invention relates to a liquid-phase epoxidation process using a mixed catalyst system to produce epoxides from hydrogen, oxygen, and olefins wherein the liquid-phase system contains a buffer. The mixed catalyst system contains a titanium zeolite and noble metal catalyst. Surprisingly, the use of a buffer in the process results in decreased ring-opening to unwanted glycols and glycol ethers in olefin epoxidation and also typically improves the activity of the process.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide oxidizing agent, such as ethyl benzene hydroperoxide or tert-butyl hydroperoxide, is commercially practiced technology. This process is performed in the presence of a solubilized molybdenum catalyst, see U.S. Pat. No. 3,351,635, or a heterogeneous titania on silica catalyst, see U.S. Pat. No. 4,367,342. Hydrogen peroxide is another oxidizing agent useful for the preparation of epoxides. Olefin epoxidation using hydrogen peroxide and a titanium silicate zeolite is demonstrated in U.S. Pat. No. 4,833,260. One disadvantage of both of these processes is the need to pre-form the oxidizing agent prior to reaction with olefin.

Another commercially practiced technology is the direct epoxidation of ethylene to ethylene oxide by reaction with oxygen over a silver catalyst. Unfortunately, the silver catalyst has not proved very useful in epoxidation of higher olefins. Therefore, much current research has focused on the direct epoxidation of higher olefins with oxygen and hydrogen in the presence of a catalyst. In this process, it is believed that oxygen and hydrogen react in situ to form an oxidizing agent. Thus, development of an efficient process (and catalyst) promises less expensive technology compared to the commercial technologies that employ pre-formed oxidizing agents.

Many different catalysts have been proposed for use in the direct epoxidation of higher olefins. For liquid-phase reactions, the catalysts typically contain palladium on a titanium zeolite support. For example, JP 4-352771 discloses the epoxidation of propylene oxide from the reaction of propylene, oxygen, and hydrogen using a catalyst containing a Group VIII metal such as palladium on a crystalline titanosilicate. The vapor-phase oxidation of olefins has been shown to produce epoxides over gold supported on titanium oxide ($Au/TiO_2$ or $Au/TiO_2$—$SiO_2$), see for example U.S. Pat. No. 5,623,090, and gold supported on titanosilicates, see for example PCT Intl. Appl. WO 98/00413.

Mixed catalyst systems for olefin epoxidation with hydrogen and oxygen have also been disclosed. For example, JP 4-352771 at Example 13 describes the use of a mixture of titanosilicate and Pd/C for propylene epoxidation. U.S. Pat. No. 6,008,388 also describes a catalyst in which palladium is typically added to a titanium zeolite to form a catalyst system, but additionally teaches that the palladium can be incorporated into a support before mixing with the zeolite. However, the only supports that are disclosed include silica, alumina, and activated carbon. In addition, copending Application Ser. No. 09/624,942 discloses a mixed catalyst system that is useful in olefin epoxidation comprising a titanium zeolite and a gold-containing supported catalyst.

One disadvantage of liquid-phase epoxidation reactions using these catalysts is that they are prone to ring-open under standard reaction conditions to form less desirable ring-opened products such as glycols or glycol ethers. The formation of these undesired by-products is especially likely to happen when water is used as the solvent.

In sum, new processes for the direct epoxidation of olefins are eeded. Particularly valuable processes would have good productivity nd selectivity to epoxides, while reducing the likelihood of ring-opening epoxides to glycols or glycol ethers.

SUMMARY OF THE INVENTION

The invention is an olefin epoxidation process that comprises reacting an olefin, oxygen, and hydrogen in a solvent in the presence of a catalyst mixture, wherein the solvent contains a buffer. The catalyst mixture comprises a titanium zeolite and a noble metal catalyst. The process is surprisingly found to produce much lower amounts of undesired glycol by-products compared to the process without use of the buffer. Surprisingly, the use of a buffer also typically improves the activity of the process.

DETAILED DESCRIPTION OF THE INVENTION

The process of the invention employs a catalyst mixture that comprises a titanium zeolite and a noble metal-containing supported catalyst. Suitable titanium zeolites are those crystalline materials having a porous molecular sieve structure with titanium atoms substituted in the framework. The choice of titanium zeolite employed will depend upon a number of factors, including the size and shape of the olefin to be epoxidized. For example, it is preferred to use a relatively small pore titanium zeolite such as a titanium silicalite if the olefin is a lower aliphatic olefin such as ethylene, propylene, or 1-butene. Where the olefin is propylene, the use of a TS-1 titanium silicalite is especially advantageous. For a bulky olefin such as cyclohexene, a larger pore titanium zeolite such as a titanium zeolite having a structure isomorphous with zeolite beta may be preferred.

Titanium zeolites comprise the class of zeolitic substances wherein titanium atoms are substituted for a portion of the silicon atoms in the lattice framework of a molecular sieve. Such substances are well known in the art.

Particularly preferred titanium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium-containing molecular sieves having framework structures isomorphous to zeolite beta, mordenite, ZSM48, ZSM-12, and MCM-41 are also suitable for use. The titanium zeolites preferably contain no elements other than titanium, silicon, and oxygen in the lattice framework, although minor amounts of boron, iron, aluminum, sodium, potassium, copper and the like may be present.

Preferred titanium zeolites will generally have a composition corresponding to the following empirical formula $xTiO_2$ $(1-x)SiO_2$ where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

The catalyst mixture employed in the process of the invention also contains a noble metal catalyst. While any noble metal catalyst can be utilized (i.e., gold, silver, platinum, palladium, iridium, ruthenium, osmium metal catalysts), either alone or in combination, palladium and gold are particularly desirable. Suitable noble metal catalysts include high surface area noble metals, noble metal alloys, and supported noble metal catalysts. Examples of suitable noble metal catalysts include high surface area palladium and palladium alloys. However, particularly preferred noble metal catalysts are supported noble metal catalysts comprising a noble metal and a support.

For supported noble metal catalysts, the support is preferably a porous material. Supports are well-known in the art. There are no particular restrictions on the type of support that are used. For instance, the support can be inorganic oxides, inorganic chlorides, carbon, and organic polymer resins. Preferred inorganic oxides include oxides of Group 2, 3, 4, 5, 6, 13, or 14 elements. Particularly preferred inorganic oxide supports include silica, alumina, titania, zirconia, niobium oxides, tantalum oxides, molybdenum oxides, tungsten oxides, amorphous titania-silica, amorphous zirconia-silica, amorphous niobia-silica, and the like. Preferred organic polymer resins include polystyrene, styrene-divinylbenzene copolymers, crosslinked polyethyleneimines, and polybenzimidizole. Suitable supports also include organic polymer resins grafted onto inorganic oxide supports, such as polyethylenimine-silica. Preferred supports also include carbon. Particularly preferred supports include carbon, silica, silica-aluminas, titania, zirconia, and niobia.

Preferably, the support has a surface area in the range of about 10 to about 700 m²/g, more preferably from about 50 to about 500 m²/g, and most preferably from about 100 to about 400 m²/g. Preferably, the pore volume of the support is in the range of about 0.1 to about 4.0 mL/g, more preferably from about 0.5 to about 3.5 mL/g, and most preferably from about 0.8 to about 3.0 mL/g. Preferably, the average particle size of the support is in the range of about 0.1 to about 500 μm, more preferably from about 1 to about 200 μm, and most preferably from about 10 to about 100 μm. The average pore diameter is typically in the range of about 10 to about 1000 Å, preferably about 20 to about 500 Å, and most preferably about 50 to about 350 Å.

The supported noble metal catalyst also contains a noble metal. While any of the noble metals can be utilized (i.e., gold, silver, platinum, palladium, iridium, ruthenium, osmium), either alone or in combination, palladium and gold are particularly desirable. Typically, the amount of noble metal present in the supported catalyst will be in the range of from 0.01 to 20 weight percent, preferably 0.1 to 5 weight percent. The manner in which the noble metal is incorporated into the supported catalyst is not considered to be particularly critical. For example, the noble metal (for example, Pd tetraamine bromide) may be supported on the support by impregnation, adsorption, ion-exchange, precipitation, or the like.

There are no particular restrictions regarding the choice of noble metal compound or complex used as the source of the noble metal in the supported catalyst. For example, suitable compounds include the nitrates, sulfates, halides (e.g., chlorides, bromides), carboxylates (e.g. acetate), and amine complexes of noble metals.

Similarly, the oxidation state of the noble metal is not considered critical. In the case of palladium for instance, the palladium may be in an oxidation state anywhere from 0 to +4 or any combination of such oxidation states. To achieve the desired oxidation state or combination of oxidation states, the noble metal compound after being introduced into the supported catalyst may be fully or partially pre-reduced. Satisfactory catalytic performance can, however, be attained without any pre-reduction.

After supported catalyst formation, the supported catalyst may be optionally thermally treated in a gas such as nitrogen, helium, vacuum, hydrogen, oxygen, air, or the like. The thermal treatment temperature is typically from about 50 to about 550° C.

The titanium zeolite and the noble metal catalyst may be used in the epoxidation process as a mixture of powders or as a mixture of pellets. In addition, the titanium zeolite and noble metal catalyst may also be pelletized or extruded together prior to use in epoxidation. If pelletized or extruded together, the catalyst mixture may additionally comprise a binder or the like and may be molded, spray dried, shaped or extruded into any desired form prior to use in epoxidation. The weight ratio of titanium zeolite:noble metal catalyst is not particularly critical. However, a titanium zeolite:noble metal catalyst ratio of 0.01–100 (grams of titanium zeolite per gram of noble metal catalyst) is preferred.

The process of the invention comprises contacting an olefin, oxygen, and hydrogen in a solvent in the presence of the catalyst mixture. Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing $C_2$–$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

The process of the invention also requires the use of a solvent. Suitable solvents include any chemical that is a liquid under reaction conditions, including, but not limited to, oxygen-containing hydrocarbons such as alcohols, aromatic and aliphatic solvents such as toluene and hexane, chlorinated aromatic and aliphatic solvents such as methylene chloride and chlorobenzene, and water. Suitable oxygenated solvents include water and oxygen-containing hydrocarbons such as alcohols, ethers, esters, ketones, and the like. Preferred oxygenated solvents include lower aliphatic $C_1$–$C_4$ alcohols such as methanol, ethanol, isopropanol, and tert-butanol, or mixtures thereof, and water. Fluorinated alcohols can be used. A preferred solvent is water. It is also possible to use mixtures of the cited alcohols with water.

The process of the invention also requires the use of a buffer. The buffer will typically be added to the solvent to form a buffer solution. The buffer solution is employed in the reaction to inhibit the formation of glycols during epoxidation. Buffers are well known in the art.

Buffers useful in this invention include any suitable salts of oxyacids, the nature and proportions of which in the mixture, are such that the pH of their solutions may range from 3 to 10, preferably from 4 to 9 and more preferably from 5 to 8. Suitable salts of oxyacids contain an anion and cation. The anion portion of the salt may include anions such as phosphate, carbonate, acetate, citrate, borate, phthalate, silicate, aluminosilicate, or the like. The cation portion of the salt may include cations such as ammonium, alkylammoniums (e.g., tetraalkylammoniums), alkali metals, alkaline earth metals, or the like. Cation examples include $NH_4$, $NBu_4$, Li, Na, K, Cs, Mg, and Ca cations. More preferred buffers include alkali metal phosphate buffers. Buffers may preferably contain a combination of more than one suitable salt. Typically, the concentration of buffer in the solvent is from about 0.0001 M to about 1 M, preferably from about 0.001 M to about 0.1 M, and most preferably from about 0.005 M to about 0.05 M.

Oxygen and hydrogen are also required for the process of the invention. Although any sources of oxygen and hydrogen are suitable, molecular oxygen and molecular hydrogen are preferred. The molar ratio of hydrogen to oxygen can usually be varied in the range of $H_2:O_2=1:100$ to $5:1$ and is especially favorable at 1:5 to 2:1. The molar ratio of oxygen to olefin is usually 1:1 to 1:20, and preferably 1:1.5 to 1:10. Relatively high oxygen to olefin molar ratios (e.g., 1:1 to 1:3) may be advantageous for certain olefins.

In addition to olefin, oxygen and hydrogen, an inert gas carrier may be preferably used in the process. As the carrier gas, any desired inert gas can be used. Suitable inert gas carriers include noble gases such as helium, neon, and argon in addition to nitrogen and carbon dioxide. Saturated hydrocarbons with 1–8, especially 1–6, and preferably with 1–4 carbon atoms, e.g., methane, ethane, propane, and n-butane, are also suitable. Nitrogen and saturated $C_1$–$C_4$ hydrocarbons are the preferred inert carrier gases. Mixtures of the listed inert carrier gases can also be used. The molar ratio of olefin to carrier gas is usually in the range of 100:1 to 1:10 and especially 20:1 to 1:10.

Specifically in the epoxidation of propylene according to the invention, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

The amount of catalyst used may be determined on the basis of the molar ratio of the titanium contained in the titanium zeolite to the olefin that is supplied per unit time. Typically, sufficient catalyst is present to provide a titanium/olefin per hour molar feed ratio of from 0.0001 to 0.1.

For the liquid-phase process of the invention, the catalyst is preferably in the form of a suspension or fixed-bed. The process may be performed using a continuous flow, semi-batch or batch mode of operation. It is advantageous to work at a pressure of 1–100 bars. Epoxidation according to the invention is carried out at a temperature effective to achieve the desired olefin epoxidation, preferably at temperatures in the range of 0–250° C., more preferably, 20–200° C.

The following examples merely illustrate the invention. Those skilled in the art will recognize many variations that are within the spirit of the invention and scope of the claims.

EXAMPLE 1

Preparation of Buffer Solutions

Preparation of Cesium Phosphate Buffer: Cesium hydroxide (22.12 g) is dissolved in deionized water (17.25 g) in a plastic beaker. In a separate container, 85% phosphoric acid (5.85 g) is added with cooling to 400 grams of deionized water. Twenty-five grams of the cesium hydroxide solution is carefully added to the phosphoric acid solution. After the addition, enough deionized water is added to the cesium phosphate buffer to give a volume of 500 mL. The pH of the solution is measured to be 6.9. Two hundred and twenty grams of the above solution (pH=6.9) is then treated with 85% phosphoric acid (1.01 g) to give a cesium phosphate buffer solution with a pH=6.02.

Preparation of Sodium Phosphate Buffer: Sodium dihydrogen phosphate (6.0 g) is dissolved into 500 grams of deionized water. Sodium hydroxide (1.2 g) is dissolved in 300 mL of deionized water in a plastic beaker. A pH=7 buffer is obtained by adding 232 grams of the sodium hydroxide solution to 400 grams of the sodium dihydrogen phosphate solution. The pH of the mixed solution is 7.02. A pH=6 buffer is obtained by adding 11.2 grams of the sodium hydroxide solution to 100 grams of the sodium dihydrogen phosphate solution. The pH of the mixed solution is 6.0.

Preparation of Potassium Phosphate Buffer: Potassium dihydrogen phosphate (6.8 g) is dissolved into 500 grams of deionized water. Potassium hydroxide (1.68 g) is dissolved in 300 mL of deionized water in a plastic beaker. A pH=7 buffer is obtained by adding 232 grams of the potassium hydroxide solution to 400 grams of the potassium dihydrogen phosphate solution. The pH of the mixed solution is 6.97. A pH=6 buffer is obtained by adding 11.2 grams of the potassium hydroxide solution to 100 grams of the potassium dihydrogen phosphate solution. The pH of the mixed solution is 6.03.

Preparation of Lithium Phosphate Buffer: Lithium hydroxide (5.0 g) is dissolved in 36 grams of deionized water in a plastic beaker. In a separate container, 85% phosphoric acid (6.0 g) is added with cooling to 400 grams of deionized water. 31 grams of the lithium hydroxide solution is carefully added to the phosphoric acid solution. After the addition, enough deionized water was added to the lithium phosphate buffer to give a volume of 500 mL. The pH was measured to be 7.12.

Preparation of Magnesium Acetate Buffer: Magnesium acetate tetrahydrate (4.28 g) is added to 200 grams of deionized water. The pH of the resulting solution is 8.02.

EXAMPLE 2

Catalyst Preparation

Catalyst 2A: $Pd/Nb_2O_5$ Preparation

In a glass beaker, $Pd(NH_3)_4Br_2$ (0.64 g) is dissolved in 40 grams of deionized water. In a separate beaker, niobium oxide powder (20 g, from Reference Metals) is slurried in 90 grams of deionized water. The palladium salt solution is added to the niobium oxide slurry with stirring over a 10-minute period. The resulting slurry is stirred at 23° C. for two hours, then the solids are separated by centrifuge. The solids are washed four times by slurrying in 80 grams of water and centrifuging. The solids are then dried in a vacuum oven (1 torr) at 50° C. for 4 hours to give 14.6 grams of Catalyst 1. Elemental analysis showed palladium=1.01 wt. %, bromide =1.6 wt. %, nitrogen 0.22 wt. % and niobium=68 wt. %.

Catalyst 2B: Pd/C Preparation

In a 500-mL roundbottom flask, Acticarbone 2LS activated carbon (16 g, Elf Atochem) is slurried into deionized water (50 g) and methanol (150 mL). Palladium acetate (0.36 g) in acetone (80 mL) is then added to the carbon slurry over a 20 minute period. The resulting slurry is stirred at 50° C. for 1 hour. About half of the solvent is removed by rotoevaporation, then the slurry is filtered and the solids washed (three times with 100 mL portions of deionized water), air dried, and then dried in a vacuum oven (1 Torr) at 50° C. for 4 hours. Elemental analysis shows 0.93 wt. % palladium.

Catalyst 2C: Preparation of Pd/sulfonated C

Acticarbone 2LS activated carbon is pretreated and sulfonated according to the procedure reported in EP0978316A1 examples 1 and 2. In a 3-neck one-liter flask, concentrated hydrochloric acid (90 g, 37 weight % HCl) is slowly added to deionized water (520 g). Acticarbone 2LS activated carbon (26 g, Elf Atochem) is then added to this solution and the slurry is heated at 80° C. with mixing for 2.5 hours. After cooling to 23° C., the solids are filtered, washed (five times with 100 mL portions of deionized water), and then oven-dried at 120° C. for two hours.

The dried solids are transferred to a 3-neck 250-mL roundbottom flask. Concentrated sulfuric acid (80 mL) is then added over a five minute period. The thick slurry is heated at 140° C. for 4 hours, cooled, and transferred to a beaker containing 500 grams of deionized water. The solids are isolated by filtration, washed (eight times with 250 mL portions of deionized water), and air dried.

These solids are transferred to a three-neck 500-mL roundbottom flask and slurried in 140 grams of deionized water. Hydrogen peroxide (24 g, 30 weight percent $H_2O_2$) is then added to the slurry, followed by heating at 70° C. for two hours. After cooling to 23° C., the solids are filtered, washed (with 150 mL of deionized water), and then oven-dried at 120° C. for two hours to give 22 grams of sulfonated carbon. The slurry is cooled to 23° C., filtered and the solids washed with 150 mL of deionized water. The solids were oven dried at 120° C. for two hrs to give 22 grams of sulfonated carbon. Elemental analysis shows 80 wt. % carbon, 0.5 wt. % sulfur, 0.39 wt. % chloride, 0.2 wt. % silicon, and 0.2 wt. % nitrogen.

In a 250-mL roundbottom flask, sulfonated carbon (6 g, from above) is slurried into deionized water (10 g) and methanol (80 mL). Palladium acetate (0.14 g) in acetone (30 mL) is then added to the carbon slurry over a 5 minute period. The resulting slurry is stirred at 23° C. for 30 minutes, followed by heating at 500C for 1 hour. About half of the solvent is removed by rotoevaporation, then the slurry is filtered and the solids are washed (two times with 50 mL portions of deionized water), air dried, and then dried at 110° C. for 2 hours. Elemental analysis shows 0.89 wt. % palladium and 0.6 wt. % sulfur.

Catalyst 2D is a commercial 1.3 wt. % Pd on sodium aluminosilicate available from Sud-Chemie.

Catalyst 2E is a commercial 1 wt. % Pd on polyethylenimine-silica available from Strem Chemical.

EXAMPLE 3

Epoxidation Reactions Using TS-1 and Supported Palladium Catalysts with or without Addition of Buffer TS-1 can be made according to any known literature procedure. See, for example, U.S. Pat. No. 4,410,501, DiRenzo, et. al., *Microporous Materials* (1997), Vol. 10, 283, or Edler, et. al., *J. Chem. Soc., Chem. Comm.* (1995), 155. The TS-1 is calcined at 550° C. for 4 hours before use.

A 300 cc stainless steel reactor is charged with the supported palladium catalyst (0.2 g), TS-1 (0.5 g, titanium amount =1.6 weight %), deionized water (~120 g), and 13 grams of a buffer (if used). The reactor is then charged to 200 psig with a feed consisting of 4% hydrogen, 4% oxygen, 5% propylene, 0.5% methane and the balance nitrogen. The pressure in the reactor is maintained at 200 psig via a backpressure regulator with the feed gases passed continuously through the reactor at 1480 cc/min (measured at 23° C. and one atmosphere pressure). In order to maintain a constant solvent level in the reactor during the run, the oxygen, nitrogen and propylene feeds are passed through a two-liter stainless steel vessel (saturator) preceding the reactor, containing 1.5 liters of water. The reactor is stirred at 1600 rpm. The reaction mixture is heated to 60° C. (except for runs 3K and 3L which are run at 45° C.) and the gaseous effluent is analyzed by an online GC every hour and the liquid analyzed by offline GC at the end of the 18 hour run.

The results are summarized in Table 1 comparing runs with catalysts 2A–2E with and without addition of buffers.

EXAMPLE 4

Preparation of Au/TiO$_2$ Catalyst

Catalysts 4A and 4B: Chloroauric acid (0.25 g, Alfa Aesar) is dissolved in 400 mL of deionized water and the solution is heated to 70° C. The pH of the solution is then adjusted to pH 7.5 by the addition of 5% sodium hydroxide. Titania (10 g, Degussa P25) is added to the solution and the mixture is stirred for 1 hour before cooling to room temperature. The mixture is then filtered, and the solid is recovered and washed by stirring in 1 liter of deionized water for 10 minutes and then filtering the mixture. The recovered solid is then washed and filtered in the same manner 3 more times. The recovered solid is then dried under vacuum at room temperature for 12 hours, heated to 120° C. in air and held for 2 hours, and finally heated to 400° C. and held for 4 hours.

Catalyst 4C is prepared using the same method as described above, except that 0.75 gram of chloroauric acid is used.

EXAMPLE 5

Epoxidation of Propylene Using Catalyst Mixture of TS-1 and Au/TiO$_2$ with Buffer The catalyst mixture, containing TS-1 (1.5 g) and catalysts from example 4 (1.0 g), is slurried into 100 mL of water containing a buffer (0.01 molar $MH_2PO_4+M_2HPO_4$, M=2/1 K/Na) and added to the reactor system, consisting of a 300-mL quartz reactor and a 150-mL saturator. The slurry is then heated to 60° C. and stirred at 1000 rpm. A gaseous feed consisting of propylene, oxygen, hydrogen and the balance nitrogen is added to the system with a total flow (cc/min) and a reactor pressure (psia) that are given in Table 2. Both the gas and liquid phase samples are collected and analyzed by G.C.

Table 2 shows the reaction conditions for the epoxidation runs for Examples 5A–C. Example 5A uses Catalyst 4A, Example 5B uses Catalyst 4B, Example 5C uses Catalyst 4C.

COMPARATIVE EXAMPLE 6

Epoxidation of Propylene Using Catalyst Mixture without Buffer

Epoxidation is run according to the same procedure as Example 5 using catalyst 4B and TS-1, except that the water does not contain a buffer. Table 2 shows the reaction conditions.

The epoxidation results using the gold supported catalyst and TS-1 (see Table 3) show that the use of a buffer with the various mixed catalyst systems leads to higher productivity to PO in the epoxidation of propylene with $H_2$ and $O_2$. Also, the use of buffers results in a significant decrease in the amount of less desirable ring opened by-products as demonstrated by the increase in PO:RO (PO:ring-opened products).

COMPARATIVE EXAMPLE 7

Epoxidation of Propylene Using Pd/TS-1 with and without Buffers

A Pd/TS-1 catalyst is formed by the following procedure. In a glass beaker, $PdBr_2$ (0.38 g) is dissolved in 30% aqueous ammonium hydroxide (15 g). In a separate beaker, TS-1 (30 g, titanium amount=2.1 weight %) is slurried in 100 grams of deionized water. The palladium ammine bromide solution is then added to the TS-1 slurry over a ten minute period. The resulting slurry is stirred at 23° C. for four hours. Ten grams of the Pd/TS-1 is loaded into a quartz tube, which is placed inside a tube furnace. The solids are heated at 100° C. for four hours under a nitrogen flow (100 cc/min). Elemental analysis shows 0.4 wt. % Pd, 0.18 wt. % nitrogen, and 0.57 wt. % Br.

Epoxidation is run according to the same procedure as Example 3 using the above Pd/TS-1 catalyst in place of TS-1 and the palladium supported catalyst of Example 3, except that the reaction temperature is 45° C., the pressure is 100 psig, the run time is 20 hours, and 1.0 g of Pd/TS-1 is used. Runs with and without buffer (potassium phosphate, pH=6) are run. See Table 4 for results.

TABLE 1

Epoxidation Results for Pd/support + TS-1 Runs.

| Run # | Catalyst | Buffer | Productivity[1] | PO/POE Selectivity[2] |
|---|---|---|---|---|
| 3A | 2A | Cs phosphate pH = 7 | 0.2 | 90 |
| 3B | 2A | Cs phosphate ph = 6 | 0.26 | 91 |
| 3C | 2A | K phosphate pH = 6 | 0.17 | 50 |
| 3D | 2A | K phosphate pH = 7 | 0.13 | 92 |
| 3E | 2A | Li phosphate pH = 7 | 0.13 | 92 |
| 3F | 2A | Mg acetate pH = 8 | 0.15 | 87 |
| 3G | 2A | Na phosphate pH = 7 | 0.17 | 77 |
| 3H * | 2A | — | 0.13 | 21 |
| 3I | 2B | Cs phosphate pH = 6 | 0.17 | 76 |
| 3J * | 2B | — | 0.076 | 55 |
| 3K | 2C | Cs phosphate pH = 6 | 0.095 | 95 |
| 3L * | 2C | — | 0.07 | 60 |
| 3M | 2D | Cs phosphate pH = 6 | 0.084 | 93 |
| 3N * | 2D | — | 0.067 | 91 |
| 3O | 2E | Cs phosphate pH = 6 | 0.15 | 92 |
| 3P * | 2E | — | 0.09 | 62 |

[1]Productivity = grams POE produced/gram of catalyst per hour.
[2]PO/POE Selectivity = moles PO/(moles PO + moles propylene glycols) * 100.
* Comparative Example

TABLE 2

Reaction Conditions.

| Run # | Wt % Au | Pressure (psia) | Feed Flow Rate (mL/min) | % Propylene in feed | % H2 in feed | % O2 in feed |
|---|---|---|---|---|---|---|
| 5A | 0.66 | 15 | 110 | 9 | 6 | 3 |
| 5B | 0.64 | 90 | 452 | 13 | 4 | 4 |
| 5C | 1.53 | 15 | 110 | 10 | 6 | 3 |
| 6 * | 0.64 | 15 | 110 | 10 | 6 | 3 |

* Comparative Example

TABLE 3

Epoxidation Results.

| Run # | PO (%) | PG[1] (%) | DPG[2] (%) | Acetol (%) | HOAc (%) | $CO_2$ (%) | Propane (%) | PO/RO[3] | POE Productivity (g POE/g cat-h) |
|---|---|---|---|---|---|---|---|---|---|
| 5A | 79.4 | 10 | 3.1 | 2.6 | 4.8 | 0 | 0 | 3.9 | 0.0013 |
| 5B | 75.2 | 19.9 | 0 | 1.1 | 0 | 0 | 3.9 | 3.6 | 0.0039 |
| 5C | 63.9 | 32 | 0 | 2.7 | 1.3 | 0.1 | 0 | 1.8 | 0.0016 |
| 6* | 24.1 | 72.1 | 0 | 3.6 | 0 | 0.2 | 0 | 0.3 | 0.0027 |

*Comparative Example.
[1]PG = propylene glycol
[2]DPG = dipropylene glycol
[3]RO = Ring-Opened Products

TABLE 4

Epoxidation Results for Pd/TS-1 Runs.

| Run # | Catalyst | Buffer | Productivity[1] | PO/POE Selectivity[2] |
|---|---|---|---|---|
| 7A * | Pd/TS-1 | — | 0.14 | 82 |
| 7B * | Pd/TS-1 | K phosphate pH = 6 | 0.09 | 92 |

[1]Productivity = grams POE produced/gram of catalyst per hour.
[2]PO/POE Selectivity = moles PO/(moles PO + moles propylene glycols) * 100.
* Comparative Example

We claim:

1. A process for producing an epoxide comprising reacting an olefin, hydrogen and oxygen in a solvent in the presence of a catalyst mixture, wherein the solvent contains a buffer and the catalyst mixture comprises a titanium zeolite and a noble metal catalyst.

2. The process of claim 1 wherein the titanium zeolite is titanium silicalite.

3. The process of claim 2 wherein the titanium zeolite is TS-1.

4. The process of claim 1 wherein the noble metal catalyst is a noble metal supported catalyst comprising a noble metal and a support.

5. The process of claim 4 wherein the noble metal is selected from the group consisting of palladium and gold.

6. The process of claim 4 wherein the supported catalyst is comprised of from 0.01 to 10 weight percent noble metal.

7. The process of claim 4 wherein the support is carbon, titania, zirconia, niobium oxides, silica, alumina, silica-alumina, tantalum oxides, molybdenum oxides, tungsten oxides, titania-silica, zirconia-silica, niobia-silica, and mixtures thereof.

8. The process of claim 1 wherein the solvent is an oxygenated solvent.

9. The process of claim 8 wherein the oxygenated solvent is selected from the group consisting of alcohols, ethers, esters, ketones, water, and mixtures thereof.

10. The process of claim 1 wherein the olefin is a $C_2$–$C_6$ olefin.

11. The process of claim 10 wherein the olefin is propylene.

12. The process of claim 1 wherein the buffer comprises an anion and a cation, where the anion is selected from the group consisting of phosphate, carbonate, acetate, citrate, borate, phthalate, silicate, and aluminosilicate and the cation is selected from the group consisting of ammonium, alkylammoniums, alkali metals, and alkaline earth metals.

13. The process of claim 12 wherein the anion is a phosphate.

14. A process comprising reacting propylene, hydrogen and oxygen in water in the presence of a catalyst mixture, wherein the water contains a buffer and the catalyst mixture comprises a titanium silicalite and a supported catalyst comprising a palladium and a support.

15. The process of claim 14 wherein the titanium silicalite is TS-1.

16. The process of claim 14 wherein the supported catalyst is comprised of from 0.01 to 10 weight percent palladium.

17. The process of claim 14 wherein the support is carbon, titania, zirconia, niobium oxides, silica, alumina, silica-alumina, tantalum oxides, molybdenum oxides, tungsten oxides, titania-silica, zirconia-silica, niobia-silica, and mixtures thereof.

18. The process of claim 14 wherein the buffer comprises an anion and a cation, where the anion is selected from the group consisting of phosphate, carbonate, acetate, citrate, borate, phthallate, silicate, and aluminosilicate and the cation is selected from the group consisting of ammonium, alkylammoniums, alkali metals, and alkaline earth metals.

19. The process of claim 18 wherein the buffer is cesium phosphate.

20. The process of claim 14 further comprising a carrier gas selected from the group consisting of helium, neon, argon, nitrogen, carbon dioxide, and $C_{1-8}$ saturated hydrocarbons.

* * * * *